(12) United States Patent
Russell et al.

(10) Patent No.: US 9,212,974 B2
(45) Date of Patent: Dec. 15, 2015

(54) SELF CONTAINED SAMPLING AND PROCESSING FACILITY

(71) Applicant: Lewis Australia Pty Ltd, Moorabbin Victoria (AU)

(72) Inventors: Steven Denis Russell, Fairfield (AU); John Adrian Calvi, Bentleigh (AU)

(73) Assignee: LEWIS AUSTRALIA PTY LTD (AU)

( * ) Notice: Subject to any disclaimer, the term of this patent is extended or adjusted under 35 U.S.C. 154(b) by 464 days.

(21) Appl. No.: 13/689,903

(22) Filed: Nov. 30, 2012

(65) Prior Publication Data
US 2013/0327159 A1 Dec. 12, 2013

(30) Foreign Application Priority Data
Dec. 2, 2011 (AU) ................................ 2011905023

(51) Int. Cl.
*G01N 1/02* (2006.01)
*E21B 49/02* (2006.01)
*E21B 7/00* (2006.01)
*G01N 1/08* (2006.01)

(52) U.S. Cl.
CPC *G01N 1/02* (2013.01); *E21B 7/005* (2013.01); *E21B 49/02* (2013.01); *G01N 1/08* (2013.01)

(58) Field of Classification Search
CPC ............ G01N 1/02; G01N 1/08; E21B 7/005; E21B 49/02
USPC ............ 73/863.01, 864, 864.44, 864.45, 863, 73/864.43, 864.91
See application file for complete search history.

(56) References Cited

U.S. PATENT DOCUMENTS

| | | | | |
|---|---|---|---|---|
| 3,231,032 | A * | 1/1966 | Genberg et al. ................ | 175/171 |
| 6,377,872 | B1 * | 4/2002 | Struckman .................... | 700/258 |
| 6,386,026 | B1 * | 5/2002 | Zamfes ...................... | 73/152.04 |
| 6,855,261 | B2 * | 2/2005 | Boutte et al. .................. | 210/768 |
| 8,171,808 | B2 * | 5/2012 | Johnson et al. ............. | 73/864.43 |
| 8,214,073 | B2 * | 7/2012 | Keskinen ...................... | 700/182 |
| 2003/0182997 | A1 * | 10/2003 | Williams ................... | 73/152.23 |
| 2009/0256412 | A1 * | 10/2009 | Nieto et al. ..................... | 299/18 |
| 2010/0234993 | A1 * | 9/2010 | Seelinger et al. ............. | 700/254 |

* cited by examiner

*Primary Examiner* — Hezron E Williams
*Assistant Examiner* — Marrit Eyassu
(74) *Attorney, Agent, or Firm* — Galbreath Law Offices, P.C.; John A. Galbreath

(57) ABSTRACT

A self-contained mobile sampling and processing facility for use at a mine having at least one blast-hole that forms a blast-hole cone wherein the sampling and processing facility includes at least one primary robotic arm that carries at least one sampling tool, and the primary robotic arm and sampling tool is controlled by robotic arm and sampling tool movement controller means, and the primary robotic arm is capable of self-determining the direction, distance and shape of a nearby blast-hole cone, then subsequently positioning itself so that the sampling tool is able to engage with the blast-hole cone and retrieve a sample from it without significant mixing or stirring the cone, or a localized region of the cone, and then the sample is deposited into the processing facility.

7 Claims, 5 Drawing Sheets

SELF CONTAINED SAMPLING AND PROCESSING FACILITY

CROSS REFERENCE TO RELATED APPLICATION

This application claims priority to and benefit of Australian Provisional Patent Application No. 2011905023, filed Dec. 2, 2011, which is hereby incorporated by reference herein as if fully set forth in its entirety.

FIELD OF THE INVENTION

This invention relates to the taking of samples from blast-holes at a mine site and the processing of those samples. In particular this invention relates to mobile sampling and processing facilities that can be carried on a vehicle or towed to a blast-hole to commence operation.

BACKGROUND OF THE INVENTION

The efficient operation of an open cut mine is heavily dependent on the data collected from constant sampling to determine the concentration of ore in the sample. Traditionally where blast-holes are required as part of the mining process, sampling is done by taking multiple auger samples from each blast-hole cone, bagging them and tagging them with identification for subsequent analysis back at a lab. This data gives critical information regarding the yield and the distribution of ore so that appropriate processing of the ore can be determined. Many mines struggle to reach their full potential due in part to unreliable and inaccurate testing systems.

The current facilities consist of a centralised laboratory, sometimes servicing multiple mines. One of the critical issues concerning the laboratories inability to give reliable and accurate results relates to problems in collecting the samples from the blast-holes. Typically this is a manual operation involving a team of two workers. The team drives out to the particular area of the mine after the blast-hole drilling operation has completed, and then manually takes samples from the hole cone using a cumbersome and heavy hand held auger to perform the drilling operation in order to collect the sample. Multiple drillings of a blast-hole cone are required to improve accuracy, and the samples are collected in a bag and appropriately tagged with relevant location information.

There are a number or problems associated with this method of collecting samples:
1. Firstly, because it is a manual task, different teams can yield different results. One team may be diligent in acquiring samples from multiple locations on the blast-hole cone, while others may not. Manual operation restricts the sampling tool selection (due to ergonomic constraints) and can cause significant mixing as the tool penetrates a cone, thus causing the sample to be less representative.
2. Secondly, operation of the equipment is arduous and heavy back breaking work, also the samples collected are placed into a bag, and these typically weigh 10 to 12 kgs. As the team gets fatigued, the quality of their sampling may degrade and the quality of the sampling and the weight of the bag collected may also diminish. A smaller sample bag results in a less representative sample.
3. Thirdly, the time it takes to get a sample manually collected from the blast-hole cone, then subsequently processed and analysed at the lab is critical to maximizing the efficiency of the mine's operation. It is estimated that the time it takes to extract the relevant information from taking the sample to completing the analysis in the laboratory is from 10 to 30 hours. This time adversely affects production which in turn degrades the efficient operation of the mine.
4. Finally many mines operate in difficult and arduous regions of the Earth. Some mines operate in extreme heat and/or bitter cold. These environmental factors also may have a negative impact on the efficiency of the sample recovery teams working at the blast-hole.

Typically one team is expected to take samples from 65 to 75 blast-hole cones per shift and spend approximately 10 minutes at each hole and collect a 10 to 12 kg bag that is placed into a storage area on their vehicle for subsequent collection and delivery to the laboratory for further processing and analysis. Significant logistical effort is required in transporting the samples to the lab for analysis.

It is an object of the present invention to alleviate at least some of the problems aforementioned.

DISCLOSURE OF THE INVENTION

The present invention is a self-contained mobile sampling and processing facility for use at a mine having at least one blast-hole. The sampling and processing facility includes at least one primary robotic arm that carries at least one sampling tool. The primary robotic arm and sampling tool is controlled by robotic arm and sampling tool movement controller means. The primary robotic arm is capable of self-determining the direction, distance and shape of a nearby blast-hole cone, then subsequently positioning itself so that the sampling tool is able to engage with the blast-hole cone and retrieve a sample from it without significant mixing or stirring of the cone, or a localised region of the cone. The sample is then deposited into the processing facility.

The means that enable the primary robotic arm to self-locate the blast-hole include a camera, and a distance sensor.

Optionally the means that enable the primary robotic arm to self-locate the blast-hole may also include manual input by the operator.

One or more primary robotic arms may be carried on one or more secondary robotic arms that in combination gives extended reach and maneuverability. The robotic arms may be mounted in an inverted orientation to increase the reach and maneuverability.

The mobile sampling and processing facility is carried on a vehicle and/or towed on a trailer.

Either the primary robotic arm or the combination of primary and secondary robotic arms is capable of moving and operating on either side of the vehicle and/or towed trailer.

The processing facility includes a crusher into which the sample is deposited by the robotic arm.

The processing facility includes conveyancing means onto which the output from the crusher is fed subsequent to the crushing operation being completed.

The processing facility may include splitter means that receive the crushed sample from the conveyor means and split out a portion of the crushed sample.

The processing facility includes bagging means that receive the split out portion from the splitter means and collect it into a bag.

Preferably the bagging means is capable of receiving the sample directly from the robotic arm(s) without any preceding crushing, conveyance or splitting operations, if the operator deems that the sample is too wet for any or all of the preceding operations to be undertaken.

Preferably when the samples are wet, and the bagging means are receiving the sample directly from the robotic arm(s), the acceptable weight range of a filled sample bag is between 5 and 20 kilograms.

The robotic arm and sampling tool controller means will control at least one primary robotic arm and its associated sampling tool to continue to take samples from a variety of locations around the blast-hole cone, and continue to feed them into the processing facility until a predetermined number of samples have been taken from the blast-hole cone.

Preferably the robotic arm and sampling tool controller means includes both a manual and an automatic safety cut-out that only allows the robotic arm(s) and sampling tool(s) to be operated while the operator is within the safe confines of the vehicle cabin, and when appropriate sensor means, for example opening sensors fitted to the doors, or weight sensors in the seats, are triggered by a person alighting the vehicle during operation, or when the manual means are activated by an operator, the robotic arms and any ancillary exposed machinery is brought to a safe stop.

Preferably the facility includes proximity sensors around the vehicle that are capable of determining when a person, animal or object has moved within a safety exclusion zone around the facility during operation, thereby tripping proximity sensors which causes the robotic arm(s) and any other exposed machinery to be brought to a safe stop.

Preferably the proximity sensors include, but are not just limited to, all or a subset of video cameras, infra read detectors, RFID means, laser means, RADAR means and GPS means.

The processing facility includes weighing means that weigh the bag as it collects the split out portion.

The weighing means provide confirmation that the sample collected in the bag is within a predetermined acceptable weight range.

Alternatively the processing facility includes feedback means that are controlled by the weighing means. The feedback is sent to the robotic arm and sampling tool movement controller means so that the sampling tool will continue taking samples from the blast-hole cone in different locations relative to the blast-hole, and continue to feed them to the processing facility until the weight of the bag falls within a pre-determined acceptable weight range.

The pre-determined acceptable weight of the bag may be in the range of 1 to 5 kilograms, but more typically the acceptable weight range of the bag is between 1.8 and 1.9 kilograms.

Alternatively the sampling tool continues to take samples at different locations from the blast-hole cone and these are fed into the crusher means and the crusher means includes temporary storage means that receives the output from the crusher and holds it, thereby allowing the crushed output from multiple samples to be aggregated, before the aggregate is deposited onto the conveyance means.

Optionally the sampling tool may be an auger.

When the sampling tool is an auger, the robotic arm and sampling tool movement controller means co-ordinates the rotational speed and the rate of advancement of the auger so as to minimise any mixing of the cone, or a localised region of the cone, in order to maximise the quality of the sample taken.

The facility allows for quick interchange between sampling tools. Several tools are included in the facility for sampling different ore types. The range of tools includes but is not limited to the following augers:

a) A 100 mm nominal diameter auger with 20 mm sidewalls at a 66 mm nominal helix pitch.
b) A 150 mm nominal diameter auger with 20 mm sidewalls at a 66 mm nominal helix pitch.
c) A 150 mm nominal diameter auger with 20 mm sidewalls at a 101 mm nominal helix pitch.
d) A 200 mm nominal diameter auger with 20 mm sidewalls at a 66 mm nominal helix pitch.
e) A 200 mm nominal diameter auger with 20 mm sidewalls at a 136 mm nominal helix pitch.

Optionally any of the sampling tools have either reduced sidewalls or no sidewalls so that they are more suitable in facilitating the collection of wet samples.

Optionally, the facility includes an output storage buffer to allow the driver to remain in the vehicle for up to 1 hour before batch bagging and tagging between 10 and 20 samples.

Optionally the facility includes GPS means that enable the bag to be geotagged with relevant location data relevant to the particular blast-hole that the sample was retrieved from.

Optionally the facility includes Radio Frequency Identification (RFID) in the label that enables a particular bag to be easily identified.

The facility includes suitable batteries, and at least one DC to AC electrical inverter, and these supply all electrical power to the facility.

The batteries may be recharged by an alternator on the vehicle while the facility is in operation, and/or by including means that enable the batteries to be recharged by connection to a main power supply when the vehicle is parked at its depot.

So in accordance with the present invention a method of retrieving a sample from a blast-hole will now be described, including the steps of:

a. Driving a vehicle carrying the facility, and/or towing a trailer to the vicinity of at least one blast-hole to be sampled and parking it within the operational radius of the equipment,
b. Engaging the facility so that the robotic arm and sampling tool commence to determine the distance, direction and shape of the relevant blast-hole cone and then automatically commence taking samples from the hole cone and feeding them into the processing facility,
c. At the completion of the process, the robotic arm returns to its nominal rest state,
d. The driver retrieves the sample bag from the bagging facility and seals and tags it with appropriate identification and places it into a storage area on the vehicle,
e. The driver then places an empty bag into the bagging means, ready for the next operation on the next blasthole.

Please note that the word arm where used throughout the specification should not be limited to just a single arm, but also should be construed to include at least a pair of robotic arms on the mobile sampling and processing facility.

DETAILED DESCRIPTION OF THE PREFERRED EMBODIMENTS

Figure 1:
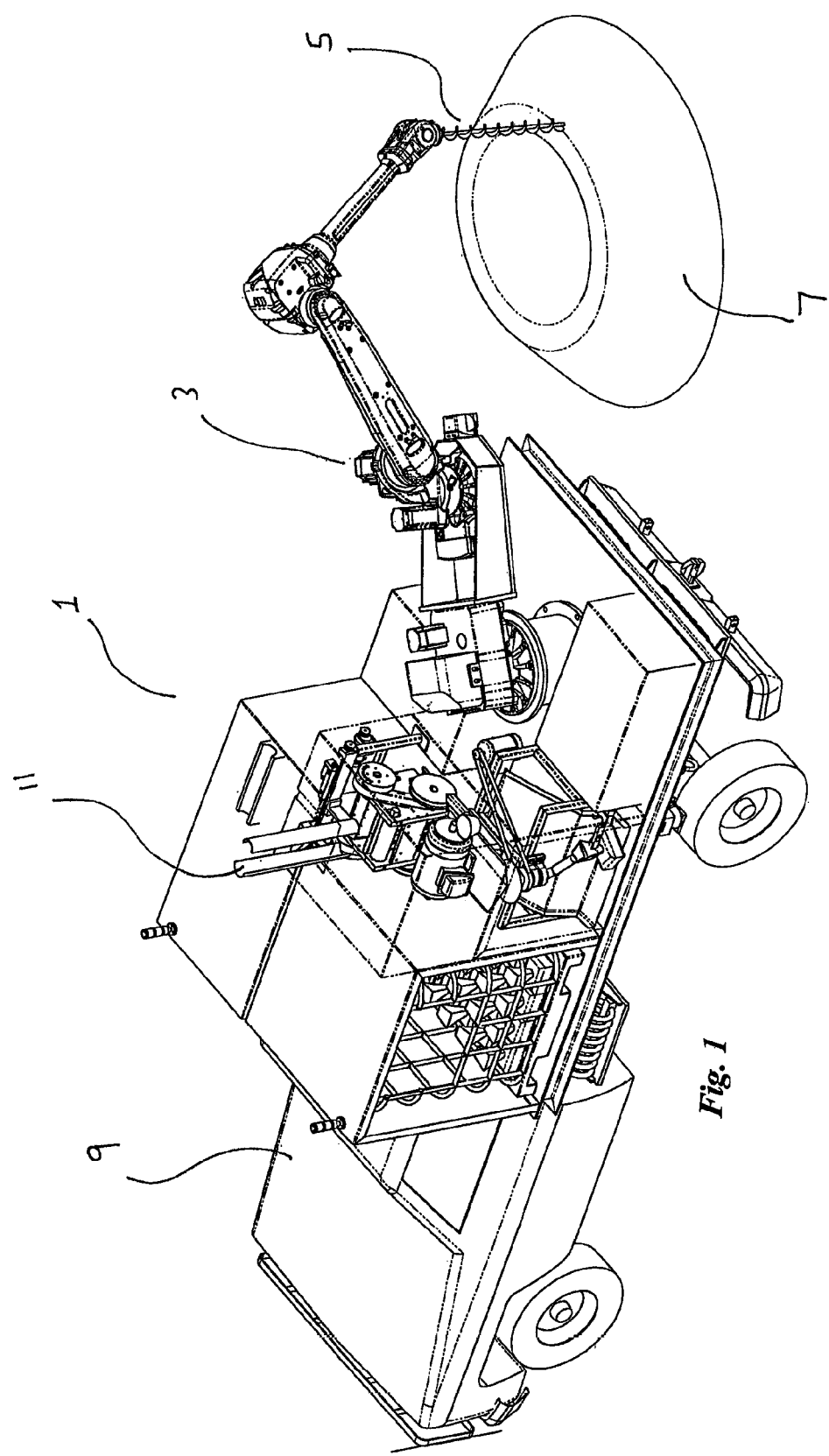
FIG. 1 shows an isometric view of a truck carrying the facility and a primary robotic arm mounted to a secondary robot arm (boom), and engaged with a nearby blast-hole.

The various elements identified by numerals in the drawings are listed in the following integer list.

Turning firstly to FIG. 1, we see shown a mobile sampling and processing facility 1 carried on a flatbed truck 9 with the sampling and processing facility mounted. It should be noted that an alternative embodiment wherein the facility is towed on a trailer also falls within the scope of the present invention. The truck 9 is parked near a blast-hole cone 7 within the operational reach of the robotic arm 3. The robotic arm 3 has self-aligned the sampling tool 5 so that the sampling tool can engage with the blast-hole cone 7 to extract a sample. This can all be initiated by the operator of the sampling and processing facility who is also the driver of the truck, while he remains seated in the vehicle. For comfort and protection from environmental hazards such as extreme hot or cold conditions, the driver is able to remain inside the air-conditioned vehicle during the majority of the operation. Upon initiation, the robotic arm 3 carrying the sampling tool 5 is able to acquire the target hole autonomously, then guide the sampling tool 5 to the vicinity of the hole 7 and determine the hole cone's size and shape. It is then able to control the position of the sampling tool relative to the hole so that the sampling tool 5 can commence retrieving samples from the blat-hole cone 7. Multiple samples from the blast-hole cone are taken at a plurality of locations around the cone 7 to improve the reliability and accuracy of the sample taken.

In this example the sampling tool 5 is illustrated as an auger, however any suitable sampling tool could be used.

After each sample taken from the blast-hole cone 7, it is then deposited in the processing facility via sampling chute 11. The sample is directed by the sampling chute 11 into the crusher where the sample is crushed down to a uniform size. The sample is then passed onto a conveyor and moved to a bagging facility. This process is repeated as more and more samples are fed into the sampling chute 11 by the sampling tool 5.

Once the predetermined number of samples has been taken from a variety of locations around the blast-hole cone 7, the sampling process is complete, and the control means for the robotic arm and sampling tool ceases to perform sampling operations, and returns the robotic arms and sampling tool to their nominal rest position in which it is ready to be transported to the next blast-hole, or to return to the laboratory sample pickup location.

Figure 4:
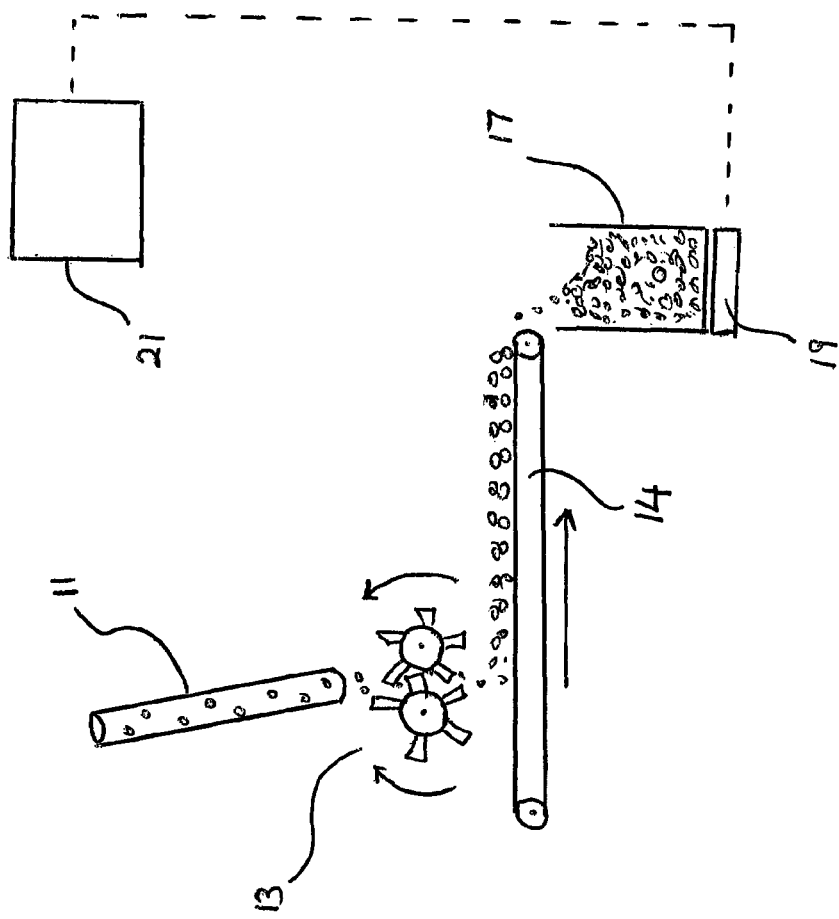
FIG. 4 shows a schematic diagram of a preferred embodiment of the sample processing system and its feedback to the robotic arm and sampling tool controller.

As best seen in FIG. 4, the facility includes weighing means 19 that weigh the sample bag 17 to ensure the weight of the sample bag 17 is within the predetermined acceptable weight range. Once this is confirmed, the bag containing the sample is then closed and labeled with the appropriate dated label/tag relating to the location from where the sample was taken. This type of labeling and tagging may include geolocation data and may also include RFID capabilities to assist in identification and retrieval of the specific sample bag.

In an alternative embodiment, the contents of the bag are continuously weighed via the weighing means 19 during the operation of the sampling facility, and the facility continues to take and process samples until the weighing means determines that the weight of the sample bag 17 falls within a predetermined acceptable weight range. Then the weighing means instructs the control means for the robotic arm and sampling tool to cease taking samples, and returns the primary robotic arm and sampling tool to their nominal rest position in which it is ready to be transported to the next blast-hole, or to return to the laboratory sample pickup location. The bag containing the weighed sample is then closed and labeled and tagged with the appropriate date relating to the location from where the sample was taken. This type of tagging may include geolocation data and may also include RFID capabilities to assist in identification and retrieval of the specific sample bag.

Figure 2:
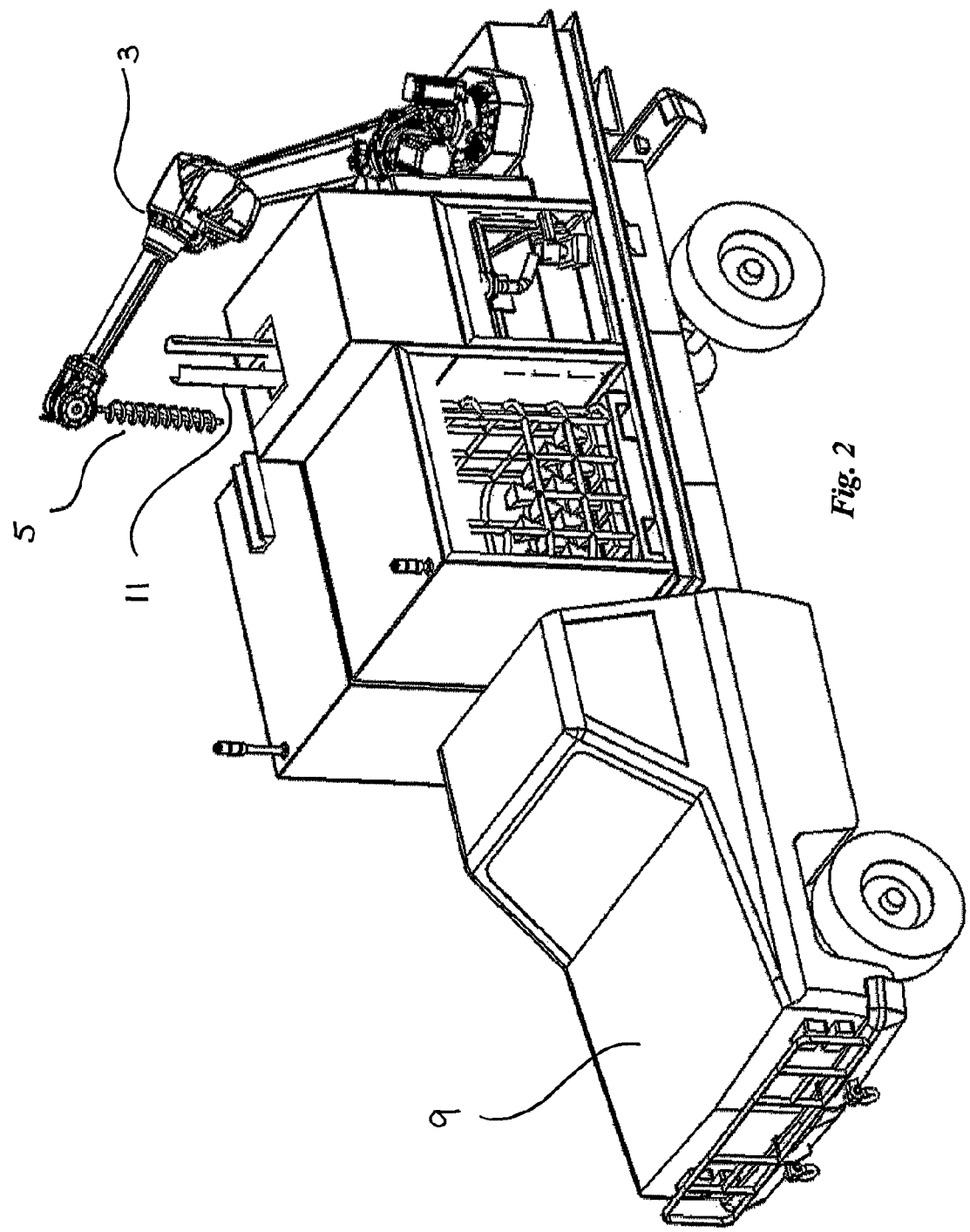
FIG. 2 shows the sample taken by the auger from the blast-hole cone being deposited into the crusher.

FIG. 2 illustrates the sampling tool preparing to deposit a sample taken from the blast-hole cone into the sampling chute 11.

Figure 3:
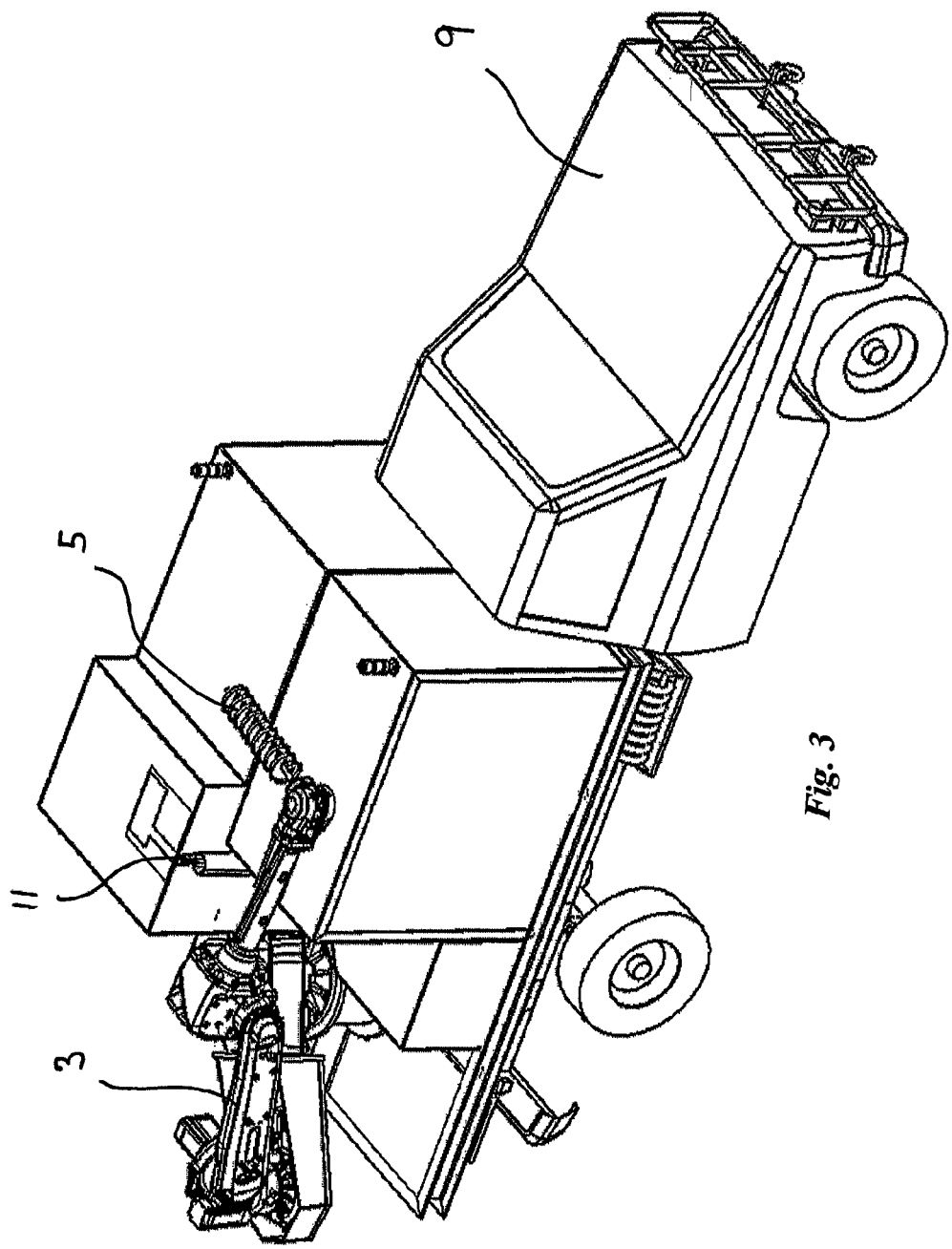
FIG. 3 shows an isometric view of a truck carrying the self-contained facility with the robotic arm and auger in their nominal rest position.

FIG. 3 illustrates the robotic arm and sampling tool in their nominal rest position ready to be transported.

Figure 5:
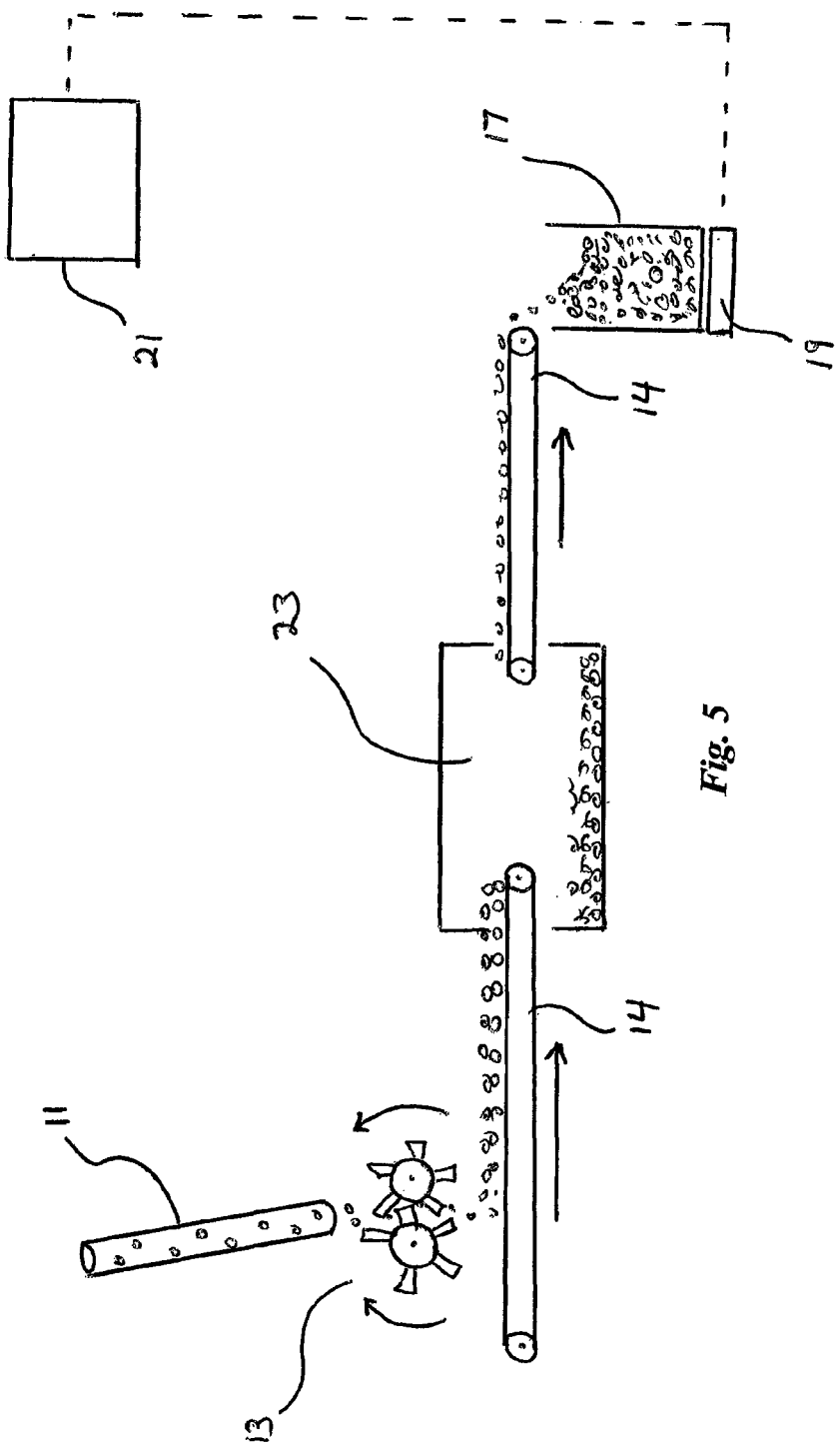
FIG. 5 shows and alternative embodiment of the sample processing system utilising splitting means.

Turning now to FIGS. 4 and 5, we can see the steps involved in processing the sample and having it bagged. The sample is first fed into a crusher 13 to ensure the sizes of the individual pieces of the sample are no greater than a set size. After the crushing stage, the sample is fed onto a conveyor means 14 and into a sample bag 17. The bag is weighed by weighing means 19 which are capable of sending a feedback signal to the robotic arm and sampling tool control means 21. When the bag reaches a set weight, the weighing means 19 instructs the robotic arm and sampling tool control means 21 to stop and move the robotic arm and sampling tool into their nominal rest position as shown in FIG. 3. The bag 17 is then sealed and tagged by the operator with relevant geolocation data and RFID enabled label.

In an alternative embodiment, a sample splitter 23, as shown in FIG. 5, is placed in the operation so that only a portion of the sample collected is bagged, while the rest of the sample is discarded. In this embodiment, more samples are required to supply the bag with enough material to reach the set weight. The advantage of this is that the bag will contain more samples taken from more places around the blast-hole cone 5, and therefore subsequent analysis of the sample included in the bag will more accurately represent the ore content at that particular blast-hole.

In another embodiment, that is more suitable when the blast-hole cone is wet, the facility may include alternative bagging means that receive the sample directly from the sampling tool without any preceding processing steps such as crushing, conveying or splitting. This mode of operation can be selected by the operator if he/she determines that the sample is too wet for crushing and/or splitting.

While the above description includes the preferred embodiments of the invention, it is to be understood that many variations, alterations, modifications and/or additions may be introduced into the constructions and arrangements of parts previously described without departing from the essential features or the spirit or ambit of the invention. It also falls within the scope of the present invention if there is an automatic sensing means, that is able to determine the moisture content of the sample, and automatically change the mode of operation for the facility when the moisture content of the sample reaches an acceptable limit. The acceptable weight range of the sample bag can also be modified inn this mode of operation so that is increased to allow for the weight of the moisture. In such cases the range may increase to between 5 and 20 kilograms.

A number of safety features can be included to protect the operator and other personnel in the area around the facility. The facility may include programmable safety controller means that help to ensure that the facility can only be operated when there is no humans, animals or other obstacles within a safety exclusion zone around the facility. Suitable sensor means, for example, cameras, infra-red sensors, RFID means, laser means and/or GPS means can send a feedback signal to the programmable safety controller, and if the sensor means detect an intrusion into the exclusion zone, it can facilitate an immediate shutdown of the facility, and cause the robotic arm to return to its nominal rest position, and all exposed machinery to cease operation. There can also be suitable sensor means within the cabin of the vehicle, such as door opening sensors of weight sensors in the seats that also shutdown the facility if it detects a person exiting the vehicle cabin during facility operation. Finally a section of strategically located manual shutdown switches can be placed on the facility and also inside the cabin to allow personnel to manually shutdown the facility if required.

It will be also understood that where the word "comprise", and variations such as "comprises" and "comprising", are used in this specification, unless the context requires otherwise such use is intended to imply the inclusion of a stated feature or features but is not to be taken as excluding the presence of other feature or features.

The reference to any prior art in this specification is not, and should not be taken as, an acknowledgment or any form of suggestion that such prior art forms part of the common general knowledge.

The claims defining the invention are as follows:

1. A self-contained mobile sampling and processing facility for use at a mine having at least one blast-hole that forms a blast-hole cone wherein the sampling and processing facility includes at least one primary robotic arm that carries at least one sampling tool, and the primary robotic arm and sampling tool is controlled by robotic arm and sampling tool movement controller means, and the primary robotic arm is adapted to self-determine the direction, distance and shape of a nearby blast-hole cone, then subsequently position itself so that the sampling tool is able to engage with the blast-hole cone and retrieve a sample from it without mixing or stirring the cone, or a localised region of the cone, and then the sample is deposited into the processing facility, and wherein the robotic arm and sampling tool movement controller means are automatic that rely on sensors including camera(s), or distance sensor(s), or manual control means by an operator, and wherein at least one primary robotic arm is carried on at least one secondary robotic arm that in combination gives extended reach and maneuverability, and the at least one robotic arm is adapted to be mounted in an inverted orientation to increase the reach and maneuverability, and wherein the mobile sampling and processing facility is carried on a vehicle or towed on a trailer, and wherein either the primary robotic arm, or the combination of primary and secondary robotic arms, is adapted to move and operate on either side of the vehicle or towed trailer, and wherein the processing facility includes all, or a subset of: a crusher into which the sample is deposited by the robotic arm, conveyancing means onto which the output from the crusher is fed subsequent to the crushing operation being completed, splitter means that receive the crushed sample from the conveying means and split out a portion of the crushed sample, bagging means that receive the split out portion from the splitter means and collect it into a bag, and wherein the bagging means is adapted to receive the sample directly from the robotic arm(s) without any preceding crushing, conveyance or splitting operations, if the operator deems that the sample is too wet for any or all of the preceding operations to be undertaken, and wherein the acceptable weight range of a filled sample bag is between 5 and 20 kilograms when the sample in the bag is wet and the bag has been filled directly by the robotic arm(s), and wherein the robotic arm and sampling tool controller means will control at least one primary robotic arm and its associated sampling tool to continue to take samples from a variety of locations around the blast-hole cone, and continue to feed them into the processing facility until a predetermined number of samples have been taken from the blast-hole cone, and wherein the robotic arm and sampling tool controller means includes both a manual and an automatic safety cut-out that only allows the robotic arm(s) and sampling tool(s) to be operated while the operator is within the safe confines of the vehicle cabin, and when appropriate sensor means, for example opening sensors fitted to the doors, or weight sensors in the seats, are triggered by a person alighting the vehicle during operation, or when the manual means are activated by an operator, the robotic arms and any ancillary exposed machinery is brought to a safe stop, and wherein the facility includes proximity sensors around the vehicle that are adapted to determine when a person, animal or object has moved within a safety exclusion zone around the facility during operation, thereby tripping the proximity sensors which causes the robotic arm(s) and any other exposed machinery to be brought to a safe stop, and wherein the proximity sensors include, but are not just limited to, all or a subset of video cameras, infra read detectors, RFID means, laser means, RADAR means and GPS means, and wherein the processing facility includes weighing means that weigh the bag as it collects the split out portion, and the weighing means are adapted to provide confirmation to the operator that the sample collected in the bag is within a predetermined acceptable weight range.

2. The self-contained mobile sampling and processing facility as claimed in claim 1 wherein the processing facility includes feedback means that are controlled by the weighing means, and the feedback is sent to the robotic arm(s) and sampling tool(s) movement controller means so that the sampling tool(s) will continue taking samples from the blast-hole cone in different locations relative to the blast-hole, and continue to feed them to the processing facility until the weight of the bag falls within a pre-determined acceptable weight range of 1 to 5 kilograms, and more typically the acceptable weight range of the bag is between 1.8 and 1.9 kilograms.

3. The self-contained mobile sampling and processing facility as claimed in claim 2 wherein the sampling tool is controlled to repeatedly cycle between taking samples at different locations from the blast-hole cone and feeding each sample into the crusher means, and the crusher means includes temporary storage means that receives the output from the crusher and holds it, thereby allowing the crushed output from multiple samples to be aggregated, before the aggregated sample is deposited onto the conveyancing means so it can pass through the additional processing steps.

4. The self-contained mobile sampling and processing facility as claimed in claim 3 wherein the sampling tool is an auger, and the robotic arm and sampling tool movement controller means co-ordinates the rotational speed and the rate of advancement of the auger so as to minimise any mixing of the blast-hole cone, or a localised region of the blast-hole cone.

5. The self-contained mobile sampling and processing facility as claimed in claim 4 wherein the facility allows for the quick interchange between sampling tools, and a plurality of tools are included in the facility for sampling different ore types, and the range of tools includes but is not limited to the following augers:
   a) a 100 mm nominal diameter auger with 20 mm sidewalls at a 66 mm nominal helix pitch, or
   b) a 150 mm nominal diameter auger with 20 mm sidewalls at a 66 mm nominal helix pitch, or
   c) a 150 mm nominal diameter auger with 20 mm sidewalls at a 101 mm nominal helix pitch, or
   d) a 200 mm nominal diameter auger with 20 mm sidewalls at a 66 mm nominal helix pitch, or
   e) a 200 mm nominal diameter auger with 20 mm sidewalls at a 136 mm nominal helix pitch,
   and any or all of the sampling tools are adapted to have either reduced sidewalls or no sidewalls so it is better suited to facilitating the collection of wet samples.

6. The self-contained mobile sampling and processing facility as claimed in claim 5 wherein the facility includes identification and tagging means that include, but are not limited to GPS means that enable the bag to be geotagged with relevant location data relevant to the particular blast-hole cone that the sample was retrieved from, Radio Frequency Identification (RFID) in the label that enables a particular bag to be easily identified.

7. The self-contained mobile sampling and processing facility as claimed in claim 6 wherein the facility includes suitable batteries, and at least one DC to AC electrical inverter, and these supply all electrical power to the facility, and the batteries are adapted to be recharged by an alternator on the vehicle while the facility is in operation, or by including means that enable the batteries to be recharged by connection to a main power supply when the vehicle is parked at its depot.

* * * * *